United States Patent [19]

Siuta et al.

[11] 4,155,930

[45] May 22, 1979

[54] UREYLENE PHENYLENE ANIONIC NAPHTHALENESULFONIC ACIDS

[75] Inventors: Gerald J. Siuta, Yonkers; Ransom B. Conrow, Pearl River; John F. Poletto, Nanuet; Seymour Bernstein, New City, all of N.Y.

[73] Assignee: American Cyanamid Company, Stamford, Conn.

[21] Appl. No.: 923,742

[22] Filed: Jul. 11, 1978

[51] Int. Cl.² .................. C07C 143/30; A61K 31/185
[52] U.S. Cl. ................................. 260/506; 260/507 R; 424/315
[58] Field of Search ......................................... 260/506

[56] References Cited

U.S. PATENT DOCUMENTS

| 1,308,071 | 7/1919 | Heymann et al. | 260/506 |
| 4,120,893 | 10/1978 | Poletto et al. | 260/506 |

*Primary Examiner*—Nicky Chan
*Attorney, Agent, or Firm*—Claude J. Caroli

[57] ABSTRACT

Novel ureylenebis[substituted-phenylenecarbonyl-(and sulfonyl)imino-substituted-phenylenesulfonylimino-naphthalenetrisulfonic acid hexaalkali metal salts], useful as inhibitors of the complement system of warm-blooded animals, the amino-substituted phenylenecarbonyl (and sulfonyl)imino-substituted-phenylenesulfonylimino-naphthalenetrisulfonic acid, trialkali metal salts, which are new intermediates for the preparation of the active ureylenes, and the process for their preparation.

13 Claims, No Drawings

UREYLENE PHENYLENE ANIONIC NAPHTHALENESULFONIC ACIDS

BACKGROUND OF THE INVENTION

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in the body processes can be found in, for example, Bull. World Health Org., 39, 935-938 (1968); Ann. Rev. Medicine, 19, 1-24 (1968); The John Hopkins Med. J., 128, 57-74 (1971); Harvey Lectures, 66, 75-104 (1972); The New England Journal of Medicine, 287, 452-454; 489-495; 545-549; 592-596; 642-646 (1972); Scientific American, 229, (No. 5), 54-66 (1973); Federation Proceedings, 32, 134-137 (1973); Medical World News, October 11, 1974, pp. 53-66; J. Allergy Clin. Immunol., 53, 298-302 (1974); Cold Spring Harbor Conf. Cell. Proliferation 2/Proteases Biol. Control/229-241 (1975); Ann. Review of Biochemistry, 44, 697 (1975); Complement in Clinical Medicine, Disease-a-Month, (1975); Complement, Scope, December 1975; Annals of Internal Medicine, 84, 580-593 (1976); "Complement: Mechanisms and Functions," Prentice-Hall, Englewood Cliffs, N.J. (1976); Essays Med. Biochem., 2, 1-35 (1976); Hospital Practice, 12, 33-43 (1977); Perturbation of Complement in Disease, Chap. 15 in Biological Amplification Systems in Immunology (Ed. Day and Good), Plenum, New York and London (1977); Am. J. Clin. Pathology, 68, 647-659 (1977).

The complement system can be considered to consist of three sub-systems: (1) a recognition unit (C1q) which enables it to combine with antibody molecules that have detected a foreign invader; (2) an activation unit (C1r, C1s, C2,C4, C3) which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is, therefore, a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969); Journal of Immunology, 119, 1-8, 1195, 1358-1364, 1482 (1977).

A variety of substances have been disclosed as inhibiting the complement system, i.e., as complement inhibitors. For example, the compounds 3,3'-ureylenebis[6-(2-amino-8-hydroxy-6-sulfo-1-naphthylazo)benzenesulfonic acid], tetrasodium salt (chlorazol fast pink), heparin and a sulphated dextran have been reported to have an anticomplementary effect, British Journal of Experimental Pathology, 33, 327-339 (1952). German Pat. No. 2,254,893 or South African Patent No. 727,923 discloses certain 1-(diphenylmethyl)-4-(3-phenylallyl)piperazines useful as complement inhibitors. Other chemical compounds having complement inhibiting activity are disclosed in, for example, Journal of Medicinal Chemistry, 12, 415-419; 902-905; 1049-1052; 1053-1056 (1969); Canadian Journal of Biochemistry, 47, 547-552 (1969); The Journal of Immunology, 104, 279-288 (1970); The Journal of Immunology, 106, 241-245 (1971); The Journal of Immunology, 111, 1061-1066 (1973); Biochim. Biophys. Acta, 317, 539-548 (1973); Life Sciences, 13, 351-362 (1973); Journal of Immunology, 113, 584 (1974); Immunology, 26, 819-829 (1974); Journal of Medicinal Chemistry, 17, 1160-1167 (1974); Biochim. Biophys. Res. Comm., 67, 225-263 (1975); Ann. N.Y. Acad. Sci., 256, 441-450 (1975); Journal of Medicinal Chemistry, 19, 634-639, 1079 (1976); Journal of Immunology, 118, 466 (1977); Arch. Int. Pharmacodyn., 226, 281-285 (1977); Biochem. Pharmacol. 26, 325-329 (1977); Journal Pharm. Sci., 66, 1367-1377 (1977); Chem. Pharm. Bull. 25, 1202-1208 (1977); Biochim. Biophys. Acta, 484, 417-422 (1977) and Journal Clin. Microbiology, 5, 278-284 (1977).

It has been reported that the known complement inhibitors epsilon-aminocaproic acid and tranexamic acid have been used with success in the treatment of hereditary angioneurotic edema, a disease state resulting from an inherited deficiency or lack of function of the serum inhibitor of the activated first component of complement (C1 inhibitor), The New England Journal of Medicine, 286, 808–812 (1972), 287, 452–454 (1972); Ann. Intern. Med., 84, 580–593 (1976); J. Allergy and Clin. Immunology, 60, 38–40 (1977).

It has also been reported that the drug pentosanpolysulfoester has an anticomplementary activity on human serum, both in vitro and in vivo, as judged by the reduction in total hemolytic complement activity; Pathologie Biologie, 25, 33–36, 25 (2), 105–108, 25 (3), 179–184 (1977).

It is known that the compound Suramin is moderately active as a complement inhibitor, and possesses the structure:

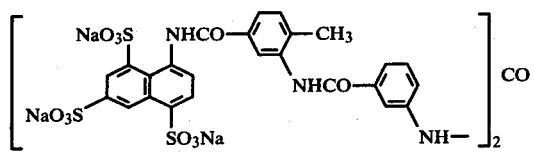

It now has been discovered that certain modifications of this structure provide compounds with enhanced inhibitory activity. This invention is based on such modifications.

The following publications, pertaining to the chemistry of Suramin, are related to the preparation of the novel compounds of this invention:

Bayer & Co., D.R.P. 278,122, June 22, 1913 [C.A. 9, 1096(1915)]
Bayer & Co., D.R.P. 288,272, Jan. 23, 1914 [C.A. 10, 2279(1916)]
Bayer & Co., D.R.P. 288,273, Feb. 21, 1914 [C.A. 10, 2279(1916)]
Frdl. 12, 185–186, 191–195 (1914–1916)
Danish Pat. No. 20,743 (1915)
Austrian Pat. No. 72,298 (1916)
Austrian Pat. No. 72,303 (1916)
U.S. Pat. No. 1,218,654 (1917)
U.S. Pat. No. 1,218,655 (1917)
Austrian Pat. No. 73,381 (1917)
U.S. Pat. No. 1,308,071 (1919)
E. Fourneau, J. Tréfouel, Mme. J. Tréfouel and J. Vallee, Acad. Sci. Comp. Rend., 178, 675–676 (1924)
E. Fourneau, F. Tréfouel and J. Vallee, Ann. de L'Institut Pasteur, 38 (2), 81–114 (1924)
B. Heymann, Zeitschrift Ang. Chem., 37, 585–589 (1924)
British Pat. No. 224,849 (1925)
U.S. Pat. No. 1,606,624 (1926)
J. E. R. McDonagh, Brit. Med. J., 693–696 (1926) [Chem. Zentralblatt, 1769–1770 (1926 II)]
W. Roehl, Arch. Schiff. Trop. Hyg., 30 (1), 103–111 (1926)
Poulenc Frères, D. R. P. 427,857, April 20, 1926 [Frdl. 15, 1434–1436(1928)]
I. E. Balaban and H. King, J. Chem. Soc., 3068–3097 (1927)
H. Bauer and J. Becker, Arb. Staatsinst. Exptl. Therap., 16 pp. (1928)
U.S. Pat. No. 1,968,820 (1934)
O. Yu. Magidson, O. S. Madaeva and M. V. Rubtzov, Khim. Farm. Prom., 2, 89–94 (1935) [C.A., 30, 4492 (1936)]
U.S. Pat. No. 2,126,180 (1938)
P. Pratsi and L. Raffa, Farmaco Sci e Tec (Pavia), 1, 21–34 (1946)
A. Spinks, Biochem. J., 42, 109–116 (1948)
E. D. Wills and A. Wormall, Biochem. J., 47, 158–170 (1950)
German Patent 890,952 (1953) [C. A. 52, 14693 (1958)]
A. Adams, J. N. Ashley and H. Bader, J. Chem. Soc., 3739–3744 (1956) [C. A. 51, 4375i]

Publications related to the biological use of Suramin compounds for the purpose of inhibiting the complement system, including humans, as determined by the in vivo and in vitro testing of the blood serum of warm-blooded animals are:

B. Stuber and K. Lang, Arch. Exptl. Path. Pharmacol., 154, 41–49 (1930) [C. A. 25, 3067(1931)]
F. Klopstock, Zeitschrift fur Immunitatsforschung und experimentalle Therapie, 75, 348–354 (1932)
H. J. Schmid, Schweiz. Med. Woch., 96, 1267–1269 (1966)
K. Lauenstein, Bayer-Symposium I, 25–30 (1969)
J. S. C. Fong and R. A. Good, Clin. Exp. Immunol., 10, 127–138 (1972)
V. Eisen and C. Loveday, Br. J. Pharmac., 49, 678–687 (1973)
D. Brackertz and F. Kueppers, Allergol. Et Immunopath., 11, 163–168 (1974)
E. Raepple, H-U. Hill and M. Loos, Immunochemistry, 13 (3), 251–255 (1976)

SUMMARY OF THE INVENTION

This invention is concerned with ureylenebis[substituted-phenylenecarbonyl(and sulfonyl)imino-substituted-phenylenesulfonylimino-naphthalenetrisulfonic acids] and all pharmaceutically acceptable salts thereof, having complement inhibiting activity, which are new compounds of the general formulae:

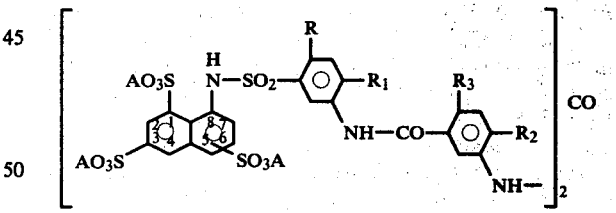

and

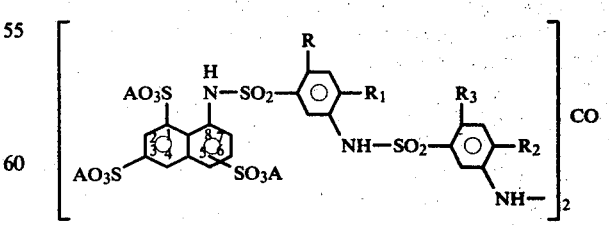

wherein R, $R_1$, $R_2$ and $R_3$ are selected from the group consisting of hydrogen and methyl; and A is a pharmaceutically acceptable salt cation.

This invention is also concerned with compounds of the formulae:

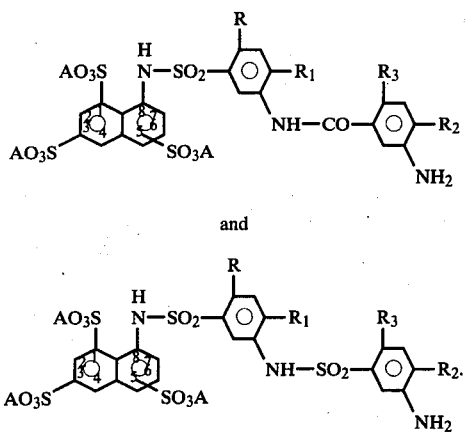

and wherein R, $R_1$, $R_2$ and $R_3$ are selected from the group consisting of hydrogen and methyl; and A is a pharmaceutically acceptable salt cation; said compounds being useful as intermediates for the preparation of the complement inhibiting compounds described above. Some of the intermediate compounds also possess complement inhibiting activity.

DESCRIPTION OF THE INVENTION

The novel intermediate amine compounds of the invention are prepared by reacting the appropriate 8-amino-1,3,5(and 1,3,6)-naphthalenetrisulfonic acid trialkali metal salt with a nitrobenzenesulfonyl chloride such as m-nitrobenzenesulfonyl chloride, 3-nitro-p-toluenesulfonyl chloride and 2-methyl-5-nitrobenzenesulfonyl chloride, for 1.5–36 hours in an aqueous solution made alkaline with alkali metal hydroxide, anhydrous alkali metal carbonate or alkali metal acetate trihydrate. After neutralization, the solution is diluted with absolute ethanol to provide the corresponding nitro-substituted-phenylenesulfonylimino-1,3,5(and 1,3,6)-naphthalenetrisulfonic acid, trialkali metal salt.

Hydrogenation of the preceding nitro trialkali metal salts using 10% palladium-carbon catalyst, filtration, concentration and treatment with absolute ethanol provides the corresponding amino-substituted-phenylenesulfonylimino naphthalenetrisulfonic acid, trialkali metal salt compounds.

The amino compounds above, dissolved in aqueous media and made alkaline with either alkali metal hydroxide or anhydrous alkali metal carbonate are reacted once more with the above listed nitrobenzenesulfonyl chloride or a nitrobenzoyl chloride such as m-nitrobenzoyl chloride or 3-nitro-p-toluoyl chloride for 1.5–36 hours. After neutralization, the solution is diluted with absolute ethanol to provide the corresponding nitro-substituted-phenylenecarbonyl (and sulfonyl-)imino-substituted-phenylenesulfonylimino-naphthalenetrisulfonic acid, trialkali metal salt.

The novel intermediate amine compounds of the invention are then obtained by hydrogenation of the above nitro compounds using 10% palladium-carbon catalyst in water as previously described, filtration and evaporation of the filtrate produces a residue which is dissolved in water and precipitated with absolute ethanol to provide the desired product.

The novel ureylene compounds of the invention, which are active complement inhibitors, are then provided by treatment of the above intermediate amine compounds with phosgene in aqueous media made alkaline with alkali metal carbonate or pyridine, neutralization, and precipitation from aqueous solution with alcohol.

This invention is concerned with a method of inhibiting the complement system in a body fluid, such as blood serum, which comprises subjecting body fluid complement to the action of an effective complement inhibiting amount of a compound encompassed within the formulae hereinabove. The method of use aspect of this invention is also concerned with a method of inhibiting the complement system in a warm-blooded animal which comprises administering to said animal an effective complement inhibiting amount of a compound encompassed within the formulae hereinabove. Body fluid can include blood, plasma, serum, synovial fluid, cerebrospinal fluid, or pathological accumulations of fluid such as pleural effusion, etc.

Compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of auto-allergic hemolytic anemia, certain kinds of platelet disorders and certain kinds of vasculitis. The compounds herein may also be used in the therapeutic treatment of warm-blooded animals having non-immunologic diseases such as paroxysmal nocturnal hemoglobinuria, hereditary angioneurotic edema (treated with Suramin, etc.) and inflammatory states induced by the action of bacterial or lysosomal enzymes on the appropriate complement components as for example, inflammation following coronary occlusion. They may also be useful in the treatment of transplant rejection and as blood culture or transport mediums.

The compounds of the present invention may be administered internally, e.g., orally, or parenterally, e.g., intra-articularly, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

While in general the sodium salts of the acids of the invention are suitable for parenteral use, other sadts may also be prepared, such as those of primary amines, e.g., ethylamine; secondary amines, e.g., diethylamine or diethanol amine; tertiary amines, e.g., pyridine or triethylamine or 2-dimethylaminomethyldibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore, as well as the sodium salt, those of the alkali metals, such as potassium and lithium; of ammonia; and of the alkaline earth metals, such as calcium or magnesium, may be employed. It will be apparent, therefore, that these salts embrace, in general, derivatives of salt-forming cations.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Test Code 035 (C3–C9 inhibitor)—This test determines the ability of the late components of human complement (C3–C9) to lyse EAC 142 in the presence of appropriate dilutions of the test compound. An active inhibitor products EAC 142 from lysis by human C3–C9; (iii) Test Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test—Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test—Lethal shock is produced in guinea pigs by an i.v. injection of anti-Forssman antiserum and the harmonic mean death time of treated guinea pigs is compared with that of simultaneous controls; (vi) Complement Level Reduction Test—In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test—Here, appropriate amounts of the test compound are added to a pool of guinea pig serum in vitro, after which the undiluted serum capillary tube assay referred to above is run. The concentration of compound inhibiting 50% is reported.

The results appear in Table I together with results of tests code 026, 035, 036 and Cap 50, showing that the compounds of the invention possess significant activity compared to Suramin.

TABLE I

| | Biological Activities | | | |
|---|---|---|---|---|
| Compound | Cl 026* Wells | C-Late 035* Wells | Shunt Inhibition 036* Wells | Cap 50* |
| Suramin | +4** | +2** | — | 361 |
| 8,8'-[Ureylenebis[(m-phenylenesulfonyl-imino)(4-methyl-3,1-phenylenesulfonyl)-imino]]di-1,3,5-naphthalenetrisulfonic acid, hexasodium salt | +3 | +1 | N | >500 |
| 8,8'-[Ureylenebis[[(1,3-phenylenesulfonylimino)-1,3-phenylenesulfonyl]-imino]]di-1,3,6-naphthalenetrisulfonic acid, hexasodium salt | +4 | +5 | +1** | >500 |
| 8,8'-[Ureylenebis[[[(6-methyl-3,1-phenylene)sulfonyl]imino]-[[(6-methyl-3,1--phenylene)sulfonyl]imino]]]di-1,3,6--naphthalenetrisulfonic acid, hexasodium salt | +3 | +1 | N | >500 |

*Code designation for tests employed as referred herein.
**Activity in wells a serial dilution assay. Higher well number indicates higher activity. The serial dilutions are two-fold.
N = Negative (no activity)

DETAILED DESCRIPTION OF THE INVENTION

EXAMPLE 1

8-(3-Metanilamido-p-toluenesulfonamido)-1,3,5-naphthalenetrisulfonic acid, trisodium salt A mixture of 25.0 g of p-toluenesulfonic acid and 95.0 ml of concentrated nitric acid is heated on a steam bath for 30 minutes. The solution is poured into 250 ml of water and evaporated at reduced pressure. A small quantity of water is added and the mixture is evaporated again. This step is repeated two additional times to remove all of the nitric acid. The mixture is neutralized with a saturated solution of sodium carbonate and evaporated affording a yellow solid. The solid is slurried with absolute ethanol, collected by filtration and washed twice with both ethanol and ether to give 10.3 g of product. The filtrate is allowed to stand and the solid formed is collected and washed as above to provide 10.0 g of additional product and a total of 20.3 g of 3-nitro-p-toluenesulfonic acid, sodium salt.

A mixture of 20.0 g of the above compound, 250 ml of thionyl chloride and 20.0 ml of dimethylformamide is refluxed for 16 hours. The excess thionyl chloride is removed by distillation, then the mixture is cooled and ether is added. The mixture is evaporated and the crude product is distilled under vacuum. The fraction recovered at a pressure of 1.0–1.5 mm of mercury and a boiling point of 152°–154° C. provides 11.5 g of 3-nitro-p-toluenesulfonyl chloride.

To a warm solution of 106.4 g of (80.5%) 8-amino-1,3,5-naphthalenetrisulfonic acid in 100 ml of water and 45.0 ml of 5 N sodium hydroxide is slowly added 500 ml of absolute ethanol with vigorous stirring for 30 minutes. The mixture is cooled to room temperature and filtered. The precipitate is washed with 80% aqueous ethanol, ethanol and ether and dried in vacuo at 110° C. for 16 hours to give 103.7 g of 8-amino-1,3,5-naphthalenetrisulfonic acid, trisodium salt.

An 8.0 g portion of 3-nitro-p-toluenesulfonyl chloride is added to a stirred solution of 7.2 g of 8-amino-1,3,5-naphthalenetrisulfonic acid trisodium salt, and 1.7 g of anhydrous sodium carbonate in 30.0 ml of water with separation of an oil. The mixture is stirred for 16 hours and then is evaporated. The residue is dissolved in water and absolute ethanol is added to provide a precipitate. The product is collected and washed with ethanol and ether. The filtrate is evaporated and the residue is precipitated as above to provide additional product. A third crop is obtained from the final filtrate to provide a total of 8.6 g of 8-(3-nitro-p-toluenesulfonamido)-1,3,5-naphthalenetrisulfonic acid, trisodium salt.

A mixture of 8.0 g of 8-(3-nitro-p-toluenesulfonamido)-1,3,5-naphthalene trisulfonic acid trisodium salt, 160 ml of water and 800 mg of 10% palladium on carbon catalyst is hydrogenated on a Parr shaker until no additional hydrogen is absorbed. The resulting mixture is filtered through diatomaceous earth and the filtrate is evaporated. The residue is dissolved in hot water and filtered. The filtrate is triturated with ethanol until cloudiness persists, then is allowed to stand at room temperature for 16 hours. The mixture is filtered and the filtrate evaporated to afford a gummy material which is dissolved in a small amount of water and triturated with ethanol. An additional 200 ml of ethanol is added and the mixture is stirred for one hour to provide a solid. The solid is collected and washed with ethanol and ether to yield 4.6 g of 8-(3-amino-p-toluenesulfonamido)-1,3,5-naphthalenetrisulfonic acid, trisodium salt as a light tan powder.

To a stirred solution of 2.0 g of 8-(3-amino-p-toluenesulfonamido)-1,3,5-naphthalenetrisulfonic acid trisodium salt and 342 mg of anhydrous sodium carbonate in 10 ml of water is added 1.5 g of m-nitrobenzenesulfonyl chloride. The mixture is stirred for 16 hours. An additional 170 mg of anhydrous sodium carbonate is added followed by 750 mg of m-nitrobenzenesulfonyl chloride and the mixture is stirred for an additional 16 hours. The reaction mixture is evaporated and the residue dissolved in hot water. A product is precipitated on the addition of absolute ethanol. The product is collected, washed with ethanol and ether and dried. Additional product is collected from the filtrate and is washed and dried as above. The above fractions of product are combined and dissolved in water, then 2.5 ml of 5 N sodium hydroxide is added and the mixture is stirred for 30 minutes. The mixture is acidified with glacial acetic acid and evaporated. The residue is dissolved in hot water and precipitated with ethanol. The product is collected and washed twice with ethanol and ether and dried to yield 700 mg of 8-(3-m-nitrobenzenesulfonamido-p-toluenesulfonamido)-1,3,5-naphthalenetrisulfonic acid, trisodium salt.

A mixture of 550 mg of 8-(3-m-nitrobenzenesulfonamido-p-toluenesulfonamido)-1,3,5-naphthalenetrisulfonic acid, trisodium salt, 30.0 ml of water and 65.0 mg of 10% palladium on carbon catalyst is hydrogenated on a Parr shaker for 1.75 hours. The resulting mixture is filtered through diatomaceous earth and the filtrate is evaporated. The crude material is dissolved in a minimum of hot water andd triturated with ethanol. The resulting solid (A) is collected by filtration and washed with ethanol and ether. The filtrate is evaporated and the residue dissolved in water. Ethanol is added and the solution is evaporated to yield a white powder (B). Fractions (A) and (B) are combined and dried to yield 500 mg of the desired product.

EXAMPLE 2

8,8'-[Ureylenebis[(m-phenylenesulfonylimino)(4-methyl-3,1-phenylenesulfonyl)imino]]di-1,3,5-naphthalenetrisulfonic acid, hexasodium salt Phosgene gas is bubbled into a solution of 400 mg of the product of Example 1, 20.0 ml of water and 55.0 mg of anhydrous sodium carbonate until the reaction mixture is acidic to Congo Red indicator. The solution is neutralized with sodium carbonate then an additional 55.0 mg of sodium carbonate is added and phosgenation is repeated until the reaction mixture is acidic. The solution is neutralized with sodium carbonate and the excess sodium carbonate is decomposed with acetic acid. The reaction mixture is evaporated and the residue is dissolved in hot water and filtered. The filtrate is triturated with ethanol and allowed to cool. The precipitate formed is collected and washed with ethanol and ether then is re-precipitated from water and ethanol and collected and washed as above. The product is dried to yield 336 mg of the desired product as a tan powder.

EXAMPLE 3

8-(3-Metanilamido-p-toluenesulfonamido)-1,3,6-naphthalenetrisulfonic acid, trisodium salt Following the procedure of Example 1, employing 8-amino-1,3,6-naphthalenetrisulfonic acid provides the product of the Example.

EXAMPLE 4

8,8'-[Ureylenebis[(m-phenylenesulfonylimino)(4-methyl-3,1-phenylsulfonyl)imino]]di-1,3,6-naphthalenetrisulfonic acid, hexasodium salt Following the procedure of Example 2, phosgenation of the product of Example 3 provides the product of the Example.

EXAMPLE 5

8-[$N^3$-(m-Aminophenylsulfonyl)metanilamido]-1,3,6-naphthalenetrisulfonic acid, trisodium salt To a stirred solution of 21.9 of 8-amino-1,3,6-naphthalenetrisulfonic acid, trisodium salt and 11.4 g of anhydrous sodium carbonate in 280 ml of water is added 24.0 g of m-nitrobenzenesulfonyl chloride. The mixture is stirred at room temperature for 16 hours, then an additional 1.0 g of sodium carbonate and 2.0 g of m nitrobenzenesulfonyl chloride are added and stirring is continued for 3 hours longer. The mixture is evaporated and the residue is dissolved in 200 ml of water. A copious amount of absolute ethanol is added and the solid formed is collected and washed with ethanol and ether, then is dried to yield 26.1 g of 8-m-nitrobenzenesulfonamido-1,3,6-naphthalenetrisulfonic acid, trisodium salt.

A mixture of 26.1 g of 8-m-nitrobenzenesulfonamido-1,3,6-naphthalenetrisulfonic acid, trisodium salt, 175 ml of water and 2.09 g of palladium on carbon catalyst is hydrogenated in a Parr shaker until no additional hydrogen is absorbed. The resulting mixture is filtered through diatomaceous earth and the filtrate is evaporated. The residue is dissolved in 60.0 ml of water and, with stirring, 400 ml of absolute ethanol is added to precipitate a solid. The mixture is allowed to stir for 2 hours, then is filtered. The product is washed with absolute ethanol and ether to give 25.3 g of 8-metanilamido-1,3,6-naphthalenetrisulfonic acid, trisodium salt.

To a stirred solution of 11.26 g of 8-metanilamido-1,3,6-naphthalenetrisulfonic acid, trisodium salt and 4.72 g of anhydrous sodium carbonate in 200 ml of water is added 10.0 g of m-nitrobenzenesulfonyl chloride. The mixture is stirred for 18 hours and is filtered. A copious amount of absolute ethanol is added to the filtrate, with stirring, to provide a precipitate. The mixture is stirred for one hour, then the solid is separated and washed with absolute ethanol and ether to yield 8.9 g of 8-[$N^3$-(m-nitrophenylsulfonyl)metanilamido]-1,3,6-naphthalenetrisulfonic acid, trisodium salt.

A mixture of 8.9 g of 8-[$N^3$-(m-nitrophenylsulfonyl)metanilamido]-1,3,6-naphthalenetrisulfonic acid, trisodium salt, 90.0 ml of water and 1.0 g of 10% palladium on carbon catalyst is hydrogenated as previously described. The resulting mixture is filtered through diatomaceous earth and the filtrate is evaporated. The residue is dissolved in 25.0 ml of water, then absolute ethanol is added to precipitate the product. The precipitate is collected, is washed with ethanol and ether and dried to yield 6.1 g of the desired product.

EXAMPLE 6

8,8'-[Ureylenebis[[(1,3-phenylenesulfonylimino)-1,3-phenylenesulfonyl]imino]]di-1,3,6-naphthalenetrisulfonic acid, hexasodium salt Phosgene is bubbled into a solution of 3.95 g of the product of Example 5 and 2.6 ml of pyridine in 35.0 ml of water until acidic to Congo Red indicator paper. An additional 1.5 ml of pyridine is added and phosgene is bubbled in again until acidic. The mixture is neutralized with pyridine and is poured into 450 ml of stirred absolute ethanol to provide a gum. The supernatant is decanted, the gum is triturated with additional absolute ethanol to yield a solid (A) (1.8 g) which is collected and washed with ethanol and ether. The supernatant above is evaporated. The residue is triturated with a copious amount of absolute ethanol and filtered. The solid (B) is washed with ethanol and ether to provide 2.5 g of material.

Fractions (A) and (B) above are combined and dissolved in 25.0 ml of water. The solution is basified to pH 8–9 with 5 N sodium hydroxide then is neutralized with acetic acid. The solution is added dropwise to 400 ml of stirred absolute ethanol to yield a precipitate. Stirring is continued for one hour, then the precipitate is separated, washed with absolute ethanol and ether and dried to yield 2.0 g of the desired product.

EXAMPLE 7

8-[N$^3$-(m-Aminophenylsulfonyl)metanilamido]-1,3,5-naphthalenetrisulfonic acid, trisodium salt Following the procedure of Example 5, employing 8-amino-1,3,5-naphthalenetrisulfonic acid, trisodium salt provides the product of the Example.

EXAMPLE 8

8,8'-[Ureylenebis[[(1,3-phenylenesulfonylimino)-1,3-phenylenesulfonyl]imino]]di-1,3,5-naphthalenetrisulfonic acid, hexasodium salt Phosgenation (according to procedure of Example 6) of the product of Example 7 provides the product of the Example.

EXAMPLE 9

8-[5-(5-Amino-o-toluenesulfonamido)-o-toluenesulfonamido]-1,3,6-naphthalenetrisulfonic acid, trisodium salt To a boiling solution of 100 g of 5-nitro-o-toluenesulfonic acid in 110 ml of water is added a solution of 53.6 g of sodium chloride in 150 ml of boiling water. The reaction mixture solidifies and is heated to boiling with the addition of sufficient water to provide solution. Then some of the water is boiled off and the mixture is allowed to stand for 16 hours. The solid formed is collected and dried to yield 92.5 g of 5-nitro-o-toluenesulfonic acid sodium salt.

A mixture of 50.0 g of 5-nitro-o-toluenesulfonic acid sodium salt, 125 ml of thionyl chloride and 1.3 ml of dimethylformamide is stirred and refluxed for 3 hours. The excess thionyl chloride is distilled off and the residue is reevaporated twice with ether. The residue is extracted with ether and methylene chloride. The extracts are evaporated and the residue is dissolved in ether and filtered. The filtrate is concentrated while adding petroleum ether, then is placed in an ice box for 16 hours. The solid formed is collected and dried to yield 33.4 of 2-methyl-5-nitrobenzenesulfonyl chloride.

A mixture of 17.0 g of 8-amino-1,3,6-naphthalenetrisulfonic acid, trisodium salt, 17.5 g of 2-methyl-5-nitrobenzenesulfonyl chloride and 7.8 g of anhydrous sodium carbonate in 210 ml of water is stirred at room temperature for 18 hours, then an additional 0.5 g of sodium carbonate and 1.0 g of 2-methyl-5-nitrobenzenesulfonyl chloride is added and stirring is continued for 18 hours longer. The reaction mixture is evaporated and 100 ml of water is added with stirring. The mixture is filtered and 900 ml of absolute ethanol is added to the filtrate with stirring. The mixture is stirred for 2 hours, then the precipitate is collected, washed with ethanol and ether and dried to yield 20.8 g of 8-(5-nitro-o-toluenesulfonamido)-1,3,6-naphthalenetrisulfonic acid, trisodium salt.

A mixture of 20.0 g of 8-(5-nitro-o-toluenesulfonamido)-1,3,6-naphthalenetrisulfonic acid, trisodium salt, 90.0 ml of water and 20.0 g of 10% palladium on carbon catalyst is hydrogenated as described in Example 1. The reaction mixture is filtered through diatomaceous earth and the filtrate is evaporated. The residue is dissolved in a minimum amount of water, then is added dropwise to 800 ml of stirred absolute ethanol. The mixture is stirred for 2 hours and allowed to stand for 48 hours. A light yellow solid is collected, washed with ethanol and ether, then is dried to yield 15.0 g of 8-(5-amino-o-toluenesulfonamido)-1,3,6-naphthalenetrisulfonic acid, trisodium salt.

A mixture of 7.0 g of 8-(5-amino-o-toluenesulfonamido)-1,3,6-naphthalenetrisulfonic acid, trisodium salt, 5.35 g of 2-methyl-5-nitrobenzenesulfonyl chloride and 2.5 g of anhydrous sodium carbonate in 120 ml of water is stirred at room temperature for 7 hours, then an additional 0.5 g of sodium carbonate and 1.0 g of 2-methyl-5-nitrobenzenesulfonyl chloride is added and stirring is continued. After 16 hours, 0.5 g of sodium carbonate and 1.0 g of acid chloride is added again and stirring is continued for several hours. The reaction mixture is filtered and the filtrate is concentrated and precipitated crops isolated as formed. The product crops are combined to yield 6.0 g of 8-[5-(5-nitro-o-toluenesulfonamido)-o-toluenesulfonamido]-1,3,6-naphthalenetrisulfonic acid, trisodium salt.

A mixture of 6.0 g of 8-[5-(5-nitro-o-toluenesulfonamido)-o-toluenesulfonamido]-1,3,6-naphthalenetrisulfonic acid, trisodium salt, 70.0 ml of water and 920 mg of 10% palladium on carbon catalyst is hydrogenated as previously described. The resulting mixture is filtered through diatomaceous earth and the filtrate is evaporated. The residue is dissolved in 30 ml of water and added with stirring to 300 ml of absolute ethanol forming a gum. The supernatant is decanted and the gum is triturated with ethanol to provide a solid which is collected by filtration and washed with ethanol and ether to yield 1.4 g of product. Additional product (1.5 g) is precipitated from the supernatent above and is collected and washed as above and the filtrates above are evaporated and triturated with ethanol to provide 1.8 g of product. The above fractions are combined and dried to yield 4.15 g of the desired product.

EXAMPLE 10

8,8'-[Ureylenebis[[[(6-methyl-3,1-phenylene)sulfonyl]imino]-[[(6-methyl-3,1-phenylene)sulfonyl]imino]]]di-1,3,6-naphthalenetrisulfonic acid, hexasodium salt Phosgene gas is bubbled through a solution of 4.0 g of the product of Example 9 and 2.54 ml of pyridine in 35.0 ml of water with vigorous stirring until the solution becomes acidic to Congo Red indicator paper. An additional 1.3 ml of pyridine is added and the solution is phosgenated again until acidic to Congo Red indicator. The mixture is neutralized with pyridine and poured into 650 ml of absolute ethanol with stirring. Stirring is continued for 30 minutes and the precipitate is collected and washed with ethanol and ether. The material is dried, then is dissolved in 20 ml of water. The solution is made alkaline (pH 8–9) with 5 N sodium hydroxide, then neutralized with glacial acetic acid and added to 400 ml of absolute ethanol with stirring. The solution is concentrated to provide a precipitate. The solid is separated then washed with ethanol and ether and dried to yield 1.0 g of the desired product.

EXAMPLE 11

8-[5-(5-Amino-o-toluenesulfonamido)-o-toluenesulfonamido]-1,3,5-naphthalenetrisulfonic acid, trisodium salt Following the procedure of Example 9, employing 8-amino-1,3,5-naphthalenetrisulfonic acid, trisodium salt provides the product of the Example.

EXAMPLE 12

8,8'-[Ureylenebis[[[(6-methyl-3,1-phenylene)sulfonyl]-imino]-[[(6-methyl-3,1-phenylene)sulfonyl]imino]]]di-1,3,5-naphthalenetrisulfonic acid, hexasodium salt Following the phosgenation procedure of Example 10, the amine of Example 11 is converted into the product of the Example.

EXAMPLE 13

8-[3-(3-Amino-p-toluamido)-p-toluenesulfonamido]-1,3,5-naphthalenetrisulfonic acid, trisodium salt Following the procedure of Example 1, reaction of 8-(3-amino-p-toluenesulfonamido)-1,3,5-naphthalenetrisulfonic acid, trisodium salt with 3-nitro-p-toluoyl chloride followed by reduction with palladium on carbon catalyst provides the product of the Example.

EXAMPLE 14

8,8'-[Ureylenebis[[[(4-methyl-3,1-phenylenecarbonyl)imino](4-methyl-3,1-phenylenesulfonyl)]imino]]di-1,3,5-naphthalenetrisulfonic acid, hexasodium salt Following the procedure of Example 2, the amino product of Example 13 is treated with phosgene to produce the ureylene, the product of the Example.

EXAMPLE 15

8-[3-(3-Amino-p-toluamido)-p-toluenesulfonamido]-1,3,6-naphthalenetrisulfonic acid, trisodium salt Following the procedure of Example 1 with 8-amino-1,3,6-naphthalenetrisulfonic acid, trisodium salt provides 8-(3-amino-p-toluenesulfonamido)-1,3,6-naphthalenetrisulfonic acid, trisodium salt. Reaction of the latter with 3-nitro-p-toluoyl chloride followed by reduction with palladium on carbon catalyst provides the product of the Example.

EXAMPLE 16

8,8'-[Ureylenebis[[[(4-methyl-3,1-phenylenecarbonyl)imino](4-methyl-3,1-phenylenesulfonyl)]imino]]di-1,3,6-naphthalenetrisulfonic acid, hexasodium salt Following the procedure of Example 2, the amino product of Example 15 is treated with phosgene to produce the ureylene, the product of the Example.

EXAMPLE 17

8-[3-(3-Aminobenzamido)-p-toluenesulfonamido]-1,3,6-naphthalenetrisulfonic acid, trisodium salt Following the procedure of Example 1, reaction of 8-(3-amino-p-toluenesulfonamido)-1,3,6-naphthalenetrisulfonic acid, trisodium salt (Example 14) with 3-nitrobenzoyl chloride followed by reduction with palladium on carbon catalyst provides the product of the Example.

EXAMPLE 18

8,8'-[Ureylenebis[[(3,1-phenylenecarbonylimino)-(4-methyl-3,1-phenylenesulfonyl)]imino]]di-1,3,6-naphthalenetrisulfonic acid, hexasodium salt Following the procedure of Example 2, the amino product of Example 17 is treated with phosgene to produce the ureylene, the product of the Example.

EXAMPLE 19

8-[3-(3-Aminobenzamido)-p-toluenesulfonamido]-1,3,5-naphthalenetrisulfonic acid, trisodium salt Following the procedure of Example 1, reaction of 8-(3-amino-p-toluenesulfonamido)-1,3,5-naphthalenetrisulfonic acid, trisodium salt with 3-nitrobenzoyl chloride followed by reduction with palladium on carbon catalyst provides the product of the Example.

EXAMPLE 20

8,8'-[Ureylenebis[[(3,1-phenylenecarbonylimino)-(4-methyl-3,1-phenylenesulfonyl)]imino]]di-1,3,5-naphthalenetrisulfonic acid, hexasodium salt Following the procedure of Example 2, the amino product of Example 19 is treated with phosgene to produce the ureylene, the product of the Example.

EXAMPLE 21

8-[5-(5-Amino-o-toluamido)-o-toluenesulfonamido]-1,3,5-naphthalenetrisulfonic acid, trisodium salt Following the procedure of Example 1, reaction of 8-amino-1,3,5-naphthalenetrisulfonic acid with 5-nitro-o-toluenesulfonyl chloride provides 8-(5-nitro-o-toluenesulfonamido)-1,3,5-naphthalenetrisulfonic acid, trisodium salt, followed by reduction with palladium on carbon catalyst provides 8-(5-amino-o-toluenesulfonamido)-1,3,5-naphthalenetrisulfonic acid, trisodium salt.

The preceding product is then reacted with 5-nitro-o-toluoyl chloride to yield 8-[5-(5-amino-o-toluamido)-o-toluenesulfonamido]-1,3,5-naphthalenetrisulfonic acid, trisodium salt.

EXAMPLE 22

8,8'-[Ureylenebis[[[(6-methyl-3,1-phenylenecarbonyl)imino](6-methyl-3,1-phenylenesulfonyl)]imino]]di-1,3,5-naphthalenetrisulfonic acid, hexasodium salt Following the procedure of Example 2, the amino product of Example 21 is treated with phosgene to produce the ureylene, the product of the Example.

EXAMPLE 23

8-[5-(5-Amino-o-toluamido)-o-toluenesulfonamido]-1,3,6-naphthalenetrisulfonic acid, trisodium salt Following the procedure of Example 1, reaction of 8-amino-1,3,6-naphthalenetrisulfonic acid, with 5-nitro-o-toluenesulfonyl chloride provides 8-(5-nitro-o-toluenesulfonamido)-1,3,5-naphthalenetrisulfonic acid, trisodium salt, followed by reduction with palladium on carbon catalyst provides 8-(5-amino-o-toluenesulfonamido)-1,3,5-naphthalenetrisulfonic acid, trisodium salt.

The preceding product is then reacted with 5-nitro-o-toluoyl chloride to yield 8-[5-(5-amino-o-toluamido)-o-toluenesulfonamido]-1,3,5-naphthalenetrisulfonic acid, trisodium salt.

EXAMPLE 24

8,8'-[Ureylenebis[[[(6-methyl-3,1-phenylenecarbonyl)imino](6-methyl-3,1-phenylenesulfonyl)]imino]]di-1,3,6-naphthalenetrisulfonic acid, hexasodium salt Following the procedure of Example 2, the amino product of Example 23 is treated with phosgene to produce the ureylene, the product of the Example.

EXAMPLE 25

8-[N-(m-Aninobenzoyl)metanilamido]-1,3,5-naphthalenetrisulfonic acid, trisodium salt Following the procedure of Example 1, reaction of 8-amino-1,3,5-naphthalenetrisulfonic acid, trisodium salt with 3-nitrobenzenesulfonyl chloride provides, after reduction, 8-(metanilamido)-1,3,5-naphthalenetrisulfonic acid, trisodium salt. Treatment with m-nitrobenzoyl chloride, reducing the product therefrom provides the product of the Example.

EXAMPLE 26

8,8'-[Ureylenebis[[(3,1-phenylenecarbonylimino)-3,1-phenylenesulfonyl]imino]]di-1,3,5-naphthalenetrisulfonic acid, hexasodium salt Following the procedure of Example 2, treatment of the product of Example 25 with phosgene generates the ureylene, the product of the Example.

EXAMPLE 27

8-[N-(m-Aminobenzoyl)metanilamido]-1,3,6-naphthalenetrisulfonic acid, trisodium salt Following the procedure of Example 1, reaction of 8-amino-1,3,6-naphthalenetrisulfonic acid, trisodium salt with 3-nitrobenzenesulfonyl chloride provides, after reduction, 8-(metanilamido)-1,3,6-naphthalenetrisulfonic acid, trisodium salt. Treatment with m-nitrobenzoyl chloride, reducing the product therefrom provides the product of the Example.

EXAMPLE 28

8,8'-[Ureylenebis[[(3,1-phenylenecarbonylimino)-3,1-phenylenesulfonyl]imino]]di-1,3,6-naphthalenetrisulfonic acid, hexasodium salt Following the procedure of Example 2, treatment of the product of Example 27 with phosgene generates the ureylene, the product of the Example.

EXAMPLE 29

8-[3-(5-Amino-2,4-dimethylbenzamido)-p-toluenesulfonamido]-1,3,5-naphthalenetrisulfonic acid, trisodium salt Following the procedure of Example 1, reaction of 8-(3-amino-p-toluenesulfonamido)-1,3,5-naphthalenetrisulfonic acid, trisodium salt with 5-nitro-2,4-dimethylbenzoyl chloride generates 8-[3-(5-nitro-2,4-dimethylbenzamido)-p-toluenesulfonamido]-1,3,5-naphthalenetrisulfonic acid, trisodium salt. Reduction with palladium on carbon catalyst gives the product of the Example.

EXAMPLE 30

8,8'-[Ureylenebis[[[(4,6-dimethyl-3,1-phenylenecarbonyl)imino](4-methyl-3,1-phenylenesulfonyl)]-imino]]-di-1,3,5-naphthalenetrisulfonic acid, hexasodium salt Following the procedure of Example 2, phosgenation of the product from Example 29 provides the product of the Example.

EXAMPLE 31

8-[3-(5-Amino-2,4-dimethylbenzamido)-p-toluenesulfonamido]-1,3,6-naphthalenetrisulfonic acid, trisodium salt Following the procedure of Example 1, reaction of 8-(3-amino-p-toluenesulfonamido)-1,3,6-naphthalenetrisulfonic acid, trisodium salt with 5-nitro-2,4-dimethylbenzoyl chloride generates 8-[3-(5-nitro-2,4-dimethylbenzamido)-p-toluenesulfonamido]-1,3,6-naphthalenetrisulfonic acid, trisodium salt. Reduction with palladium on carbon catalyst gives the product of the Example.

EXAMPLE 32

8,8'-[Ureylenebis[[[(4,6-dimethyl-3,1-phenylenecarbonyl)imino](4-methyl-3,1-phenylenesulfonyl)]-imino]]-di-1,3,6-naphthalenetrisulfonic acid, hexasodium salt Following the procedure of Example 2, phosgenation of the product from Example 31 provides the product of the Example.

EXAMPLE 33

Preparation of Compressed Tablet

| Ingredient | mg/Tablet |
| --- | --- |
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 34

Preparation of Compressed Tablet - Sustained Action

| Ingredient | mg/Tablet |
| --- | --- |
| Active Compound as Aluminum Lake*, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5-30%.

EXAMPLE 35

Preparation of Hard Shell Capsule

| Ingredient | mg/Capsule |
| --- | --- |
| Active Compound | 0.5–500 |
| Lactose, Spray Dried | qs |
| Magnesium Stearate | 1–10 |

EXAMPLE 36

Preparation of Oral Liquid (Syrup)

| Ingredient | % W/V |
| --- | --- |
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 37

Preparation of Oral Liquid (Elixir)

| Ingredient | % W/V |
|---|---|
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 38

Preparation of Oral Suspension (Syrup)

| Ingredient | % W/V |
|---|---|
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 39

Preparation of Injectable Solution

| Ingredient | % W/V |
|---|---|
| Active Compound | 0.05–5 |
| Benzyl Alcohol N.F. | 0.9 |
| Water for Injection | 100.0 |

EXAMPLE 40

Preparation of Injectable Oil

| Ingredient | % W/V |
|---|---|
| Active Compound | 0.05–5 |
| Benzyl Alcohol | 1.5 |
| Sesame Oil qs ad | 100.0 |

EXAMPLE 41

Preparation of Intra-Articular Product

| Ingredient | Amount |
|---|---|
| Active Compound | 2–20 mg |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 42

Preparation of Injectable Depo Suspension

| Ingredient | % W/V |
|---|---|
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

EXAMPLE 43

Preparation of Dental Paste

| Ingredient | % W/W |
|---|---|
| Active Compound | 0.05–5 |
| Zinc Oxide | 15 |
| Polyethylene Glycol 4000 USP | 50 |
| Distilled Water qs | 100 |

EXAMPLE 44

Preparation of Dental Ointment

| Ingredient | % W/W |
|---|---|
| Active Compound | 0.05–5 |
| Petrolatum, White USP qs | 100 |

EXAMPLE 45

Preparation of Dental Cream

| Ingredient | % W/W |
|---|---|
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methylparaben USP | 0.18 |
| Propyl Paraben USP | 0.02 |
| Distilled Water qs | 100 |

EXAMPLE 46

Preparation of Topical Cream

| Ingredient | % W/W |
|---|---|
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 47

Preparation of Topical Ointment

| Ingredient | % W/W |
|---|---|
| Active Compound | 0.05–5 |
| Cholesterol | 3 |
| Stearyl Alcohol | 3 |
| White Wax | 8 |
| Petrolatum, White USP qs | 100 |

EXAMPLE 48

Preparation of Spray Lotion (non-Aerosol)

| Ingredient | % W/W |
| --- | --- |
| Active Compound | 0.05–5 |
| Isopropyl Myristate | 20 |
| Alcohol (Denatured) qs | 100 |

EXAMPLE 49

Preparation of Buccal Tablet

| Ingredient | g/Tablet |
| --- | --- |
| Active Ingredient | 0.00325 |
| 6 x Sugar | 0.29060 |
| Acacia | 0.01453 |
| Soluble Starch | 0.01453 |
| F.D. & C. Yellow No. 6 Dye | 0.00049 |
| Magnesium Stearate | 0.00160 |
|  | 0.32500 |

The final tablet will weigh about 325 mg. and may be compressed into buccal tablets in flat faced or any other tooling shape convenient for buccal administration.

EXAMPLE 50

Preparation of Lozenge

| Ingredient | g/Lozenge |
| --- | --- |
| Active Ingredient | 0.0140 |
| Kompact ® Sugar (Sucrest Co.) | 0.7138 |
| 6 × Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
|  | 1.4000 |

The ingredients are compressed into 5/8″ flat based lozenge tooling. Other shapes may also be utilized.

We claim:

1. A compound of the formula:

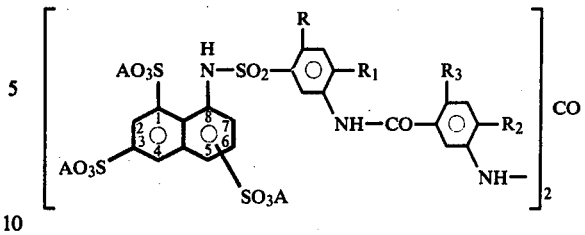

wherein R, $R_1$, $R_2$ and $R_3$ are selected from the group consisting of hydrogen and methyl; and A is a pharmaceutically acceptable salt cation.

2. A compound according to claim 1, wherein $R_1$ is methyl.

3. A compound according to claim 1, wherein $R_1$ is hydrogen.

4. The compound according to claim 1, 8,8'-[Ureylenebis[[[(4-methyl-3,1-phenylenecarbonyl)-imino](4-methyl-3,1-phenylenesulfonyl)]imino]]di-1,3,5-naphthalenetrisulfonic acid, hexasodium salt.

5. The compound according to claim 1, 8,8'-[Ureylenebis[[[(4-methyl-3,1-phenylenecarbonyl)-imino](4-methyl-3,1-phenylenesulfonyl)]imino]]di-1,3,6-naphthalenetrisulfonic acid, hexasodium salt.

6. The compound according to claim 1, 8,8'-[Ureylenebis[[(3,1-phenylenecarbonylimino)-(4-methyl-3,1-phenylenesulfonyl)]imino]]di-1,3,6-naphthalenetrisulfonic acid, hexasodium salt.

7. The compound according to claim 1, 8,8'-[Ureylenebis[[(3,1-phenylenecarbonylimino)-(4-methyl-3,1-phenylenesulfonyl)]imino]]di-1,3,5-naphthalenetrisulfonic acid, hexasodium salt.

8. The compound according to claim 1, 8,8'-[Ureylenebis[[[(6-methyl-3,1-phenylenecarbonyl)-imino](6-methyl-3,1-phenylenesulfonyl)]imino]]di-1,3,5-naphthalenetrisulfonic acid, hexasodium salt.

9. The compound according to claim 1, 8,8'-[Ureylenebis[[[(6-methyl-3,1-phenylenecarbonyl)-imino](6-methyl-3,1-phenylenesulfonyl)]imino]]di-1,3,6-naphthalenetrisulfonic acid, hexasodium salt.

10. The compound according to claim 1, 8,8'-[Ureylenebis[[(3,1-phenylenecarbonylimino)-3,1-phenylenesulfonyl]imino]]di-1,3,5-naphthalenetrisulfonic acid, hexasodium salt.

11. The compound according to claim 1, 8,8'-[Ureylenebis[[(3,1-phenylenecarbonylimino)-3,1-phenylenesulfonyl]imino]]di-1,3,6-naphthalenetrisulfonic acid, hexasodium salt.

12. The compound according to claim 1, 8,8'-[Ureylenebis[[[(4,6-dimethyl-3,1-phenylenecarbonyl)imino](4-methyl-3,1-phenylenesulfonyl)]-imino]]di-1,3,5-naphthalenetrisulfonic acid, hexasodium salt.

13. The compound according to claim 1, 8,8'-[Ureylenebis[[[(4,6-dimethyl-3,1-phenylenecarbonyl)imino](4-methyl-3,1-phenylenesulfonyl)]imino]]di-1,3,6-naphthalenetrisulfonic acid, hexasodium salt.

* * * * *